US012806596B2

(12) United States Patent
Gallagher et al.

(10) Patent No.: US 12,806,596 B2
(45) Date of Patent: Nov. 24, 2026

(54) LASER-BASED CHEMICAL PROCESSING

(71) Applicant: Orca Sciences, LLC, Kirkland, WA (US)

(72) Inventors: Patrick Gallagher, San Jose, CA (US); Ian McKay, Seattle, WA (US)

(73) Assignee: Orca Sciences, LLC, Kirkland, WA (US)

(*) Notice: Subject to any disclaimer, the term of this patent is extended or adjusted under 35 U.S.C. 154(b) by 675 days.

(21) Appl. No.: 18/376,089

(22) Filed: Oct. 3, 2023

(65) Prior Publication Data

US 2024/0109048 A1 Apr. 4, 2024

Related U.S. Application Data

(60) Provisional application No. 63/378,359, filed on Oct. 4, 2022.

(51) Int. Cl.
*B01J 19/12* (2006.01)
*B01J 19/00* (2006.01)
*C07C 5/327* (2006.01)

(52) U.S. Cl.
CPC ......... *B01J 19/121* (2013.01); *B01J 19/0013* (2013.01); *C07C 5/327* (2013.01); *B01J 2219/0869* (2013.01); *B01J 2219/0871* (2013.01); *B01J 2219/0875* (2013.01); *B01J 2219/12* (2013.01)

(58) Field of Classification Search
None
See application file for complete search history.

*Primary Examiner* — Brian W Cohen
*Assistant Examiner* — Nathanael Jason Downes
(74) *Attorney, Agent, or Firm* — Danielson Legal LLC

(57) ABSTRACT

Chemical reactors and their configuration with laser systems enable the lasers to deliver unprecedented power densities into the bulk of a suitably absorbing fluid, enabling, e.g., endothermic reactions in the gas phase, into which it may be otherwise challenging to deliver heat. These laser-based chemical reactors may be used to process a broad range of feedstocks. Two such processes involve laser-based methane pyrolysis and laser-based olefin production.

16 Claims, 6 Drawing Sheets

Front view
(emitting facets)

Side view

Front view (emitting surface)

Side view

LASER-BASED CHEMICAL PROCESSING

CROSS-REFERENCE TO RELATED APPLICATIONS

The present application claims the benefit of and priority to U.S. provisional application No. 63/378,359, filed on Oct. 4, 2022, the entire disclosure of which is hereby incorporated by reference as if set forth in its entirety herein.

TECHNICAL FIELD

Embodiments described herein generally relate to methods and systems for laser fueled chemical reactions, and more specifically to a reactor for the processing of gaseous feedstocks using laser radiation.

BACKGROUND

Traditional chemical reactors may raise the temperature of a gaseous feedstock to a suitably high temperature to cause the species in the feedstock to decompose into one or more chemical products of interest. Delivering heat to a gas using a traditional approach like a heated furnace tube is a slow process requiring long residence times of the feedstock because thermal radiation from heated tube walls is rather weak, and because the heat supplied to the fluid volume by contact with the hot tube surface is dimensionally disadvantaged. The ability of a furnace tube to efficiently process a feedstock may be further reduced by the buildup of solid reaction products (e.g., coke) on the tube walls, which restricts fluid flow and further diminishes heat transfer to the feedstock.

For example, traditional steam crackers carry out the pyrolysis of alkanes (e.g., ethane) to olefins (e.g., ethylene, propylene). The pyrolysis reaction initiates at high temperatures, but if high temperature is held for too long, the olefins themselves start to degrade to products like acetylene and soot. Hence the highest yields of olefins are obtained when the process gas is very rapidly ramped and quenched; a typical steam cracker ramps its process gas from ~600 C to ~850° C. over a few hundred milliseconds, and quenches back down to 500-600° C. within another hundred milliseconds or so.

In order to achieve such a rapid temperature ramp with high feedstock throughput—a task which is made more challenging owing to the considerable enthalpy of reaction (>100 kJ/mol $C_2H_6$) that must be delivered, as well as the rather low thermal conductivity of the gas—a steam cracker will push the process gas near the speed of sound through long (10-100 m), narrow (~10 cm diameter) "cracking coils" maintained at a high temperature (e.g., 1000° C.) by a firebox.

A severe drawback of this scheme is its susceptibility to coke deposition. Since the coils must be particularly hot (hotter than the process gas) in order to rapidly supply heat, they act as excellent nucleation sites for coke deposition. And since coke is a poor thermal conductor, the temperature of the coils must be further increased once coke starts to deposit. Increasing temperature decreases coil lifetime, and this can only continue for so long before it becomes economically advantageous to shut down the entire steam cracker to clean out the coke. The shutdown may cost two days and may happen once every few weeks to few months, depending on the length of coil (shorter coils may reduce residence time and improve yield, but may require higher temperatures and therefore coke faster). Decoking shutdowns are a major operational expense to go along with the capital expense from the massive fireboxes, long coils, and powerful pumps that drive the large fluid impedance.

As the above example illustrates, there is a need for improved chemical reactors that address the deficiencies of prior art approaches.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

Embodiments described herein relate to reactors that heat feedstocks using laser radiation (i.e., lasers), thereby rapidly delivering power into the bulk of a fluid, typically a gas. Such delivery may be very challenging by traditional means (e.g., because heat transfer into a gas via hot reactor walls is comparatively quite slow). In principle, any feedstock with optical absorption features that match the laser wavelengths at the required temperatures, pressures, and optical path lengths may be used.

In one aspect, embodiments relate to a laser reactor for processing gaseous feedstocks, the reactor having a reaction chamber with an intake for receiving a gaseous feedstock, an optical window, and an outlet; and a laser module. The laser module is configured to emit laserlight into the chamber through the window and thereby convert the gaseous feedstock into at least one reaction product.

In various embodiments the reactor further includes a receptacle for collecting the at least one reaction product as it is formed.

In various embodiments the laser module is operated in a pulsed mode.

In various embodiment the reactor further includes a plurality of optical windows and a plurality of laser modules, with each laser module of the plurality configured to emit laser light into the chamber through an optical window of the plurality of optical windows. The plurality of laser modules may be configured to surround the reaction chamber. The intake may be positioned between two windows.

In various embodiments the laser module is an array of semiconductor laser diode bars or a vertical-cavity surface-emitting laser array.

In various embodiments the reactor further includes a mechanism for adjusting the pressure of the reactor.

In various embodiments the intake is juxtaposed with the window.

In various embodiments the reaction chamber is transparent.

In various embodiments the laser light is near-infrared.

In various embodiments the gaseous feedstock includes one or more of methane, ethane, hydrogen or steam.

In various embodiments the window is optically coated to block a predetermined range of frequencies.

In various embodiments the reactor further includes a heat exchanger at the outlet.

In another aspect, embodiments relate to a method for laser processing of gaseous feedstocks. The method includes providing a reaction chamber having an intake for receiving a gaseous feedstock, an optical window, and an outlet; admitting a gaseous feedstock to the reaction chamber via the intake; and applying laser light to the gaseous feedstock through the optical window to form at least one reaction product.

In various embodiments the method further includes collecting, in a receptacle, the at least one reaction product as it is formed.

In various embodiments the reactor further includes a plurality of optical windows, and applying laser light to the gaseous feedstock includes applying laser light to the gaseous feedstock through the plurality of optical windows.

In various embodiments the method further includes increasing the pressure of the reaction chamber to improve the absorption of the laser light by the gaseous feedstock.

In various embodiments the feedstock includes one or more of methane, ethane, or naphtha.

In various embodiments the method further includes admitting an etchant gas to the reaction chamber to facilitate the cleaning of the optical window.

BRIEF DESCRIPTION OF DRAWINGS

Non-limiting and non-exhaustive embodiments of this disclosure are described with reference to the following figures, wherein like reference numerals refer to like parts throughout the various views unless otherwise specified.

DETAILED DESCRIPTION

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

The price for laser systems that are bright, efficient (>50%), and long-lasting (i.e., 10-20 years) is rapidly declining, approaching a regime in which the cost of the electricity to operate a laser could dwarf its capital expense. In such a technoeconomic landscape, lasers should become a viable option for electrified chemical or materials processing.

Embodiments of the present invention concern chemical reactors and their configuration with laser systems to enable the lasers to deliver unprecedented power densities into the bulk of a suitably absorbing fluid, which should be a broadly useful capability for performing chemical reactions (e.g., endothermic reactions in the gas phase, into which it may be otherwise challenging to deliver heat). These novel laser-based chemical reactors may be used to process a broad range of feedstocks. Two such novel processes, described below, involve laser-based methane pyrolysis and laser-based olefin production.

Laser Sources

Figure 1:
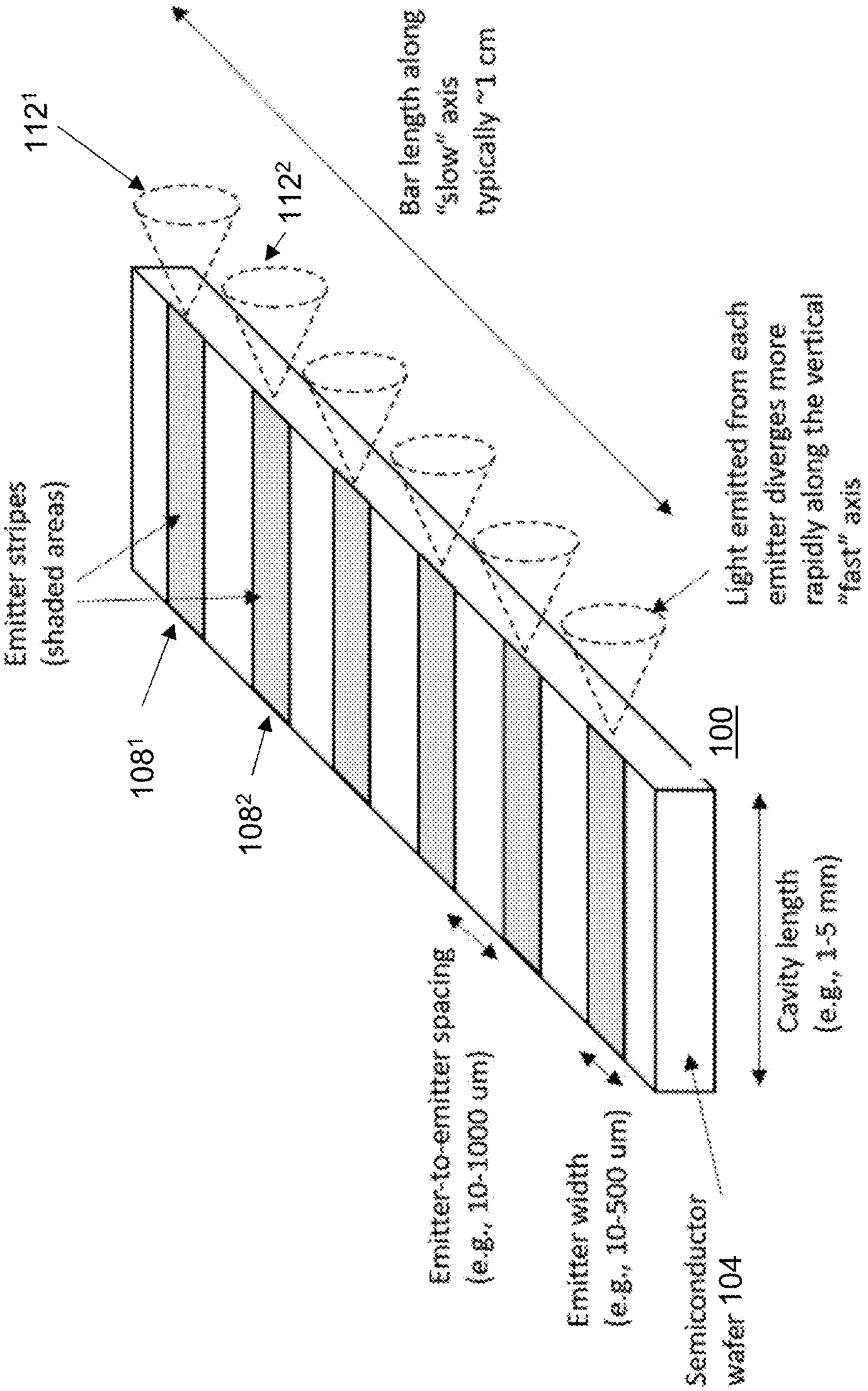
FIG. 1 depicts an exemplary semiconductor laser diode bar.

One laser source that is of particular interest for low-cost laser processing is the semiconductor laser diode bar, illustrated in FIG. 1. A diode bar 100 is a piece of specialized semiconductor wafer 104 patterned to create a one-dimensional array of "emitters" 108$^N$ (shaded for contrast), each of which constitutes a separate laser emitting a separate beamlet 112$^N$ (depicted as cones), commonly in the near-infrared. The length of the bar 100 (also the cavity length) is often around one or several mm long, although other lengths are possible. The laser cavity of each emitter 108$^N$ (typically a Fabry-Perot cavity) is often formed by the cleaved facets of the semiconductor wafer 104, which may be coated to tailor the reflection coefficient. The coatings are often chosen such that beamlets 112$^N$ emerge from only one of the two facets of the semiconductor piece 104.

The width of each emitter 108$^N$ in the periodic direction of the array 100 is usually considerably larger than a wavelength, e.g., 10-500 μm, whereas the height of each emitter (i.e., the vertical direction in FIG. 1) is typically small enough to confine a single optical mode in that dimension. The net result is that the beam 112$^N$ emerging from each emitter 108$^N$ often has considerable divergence (e.g., 40 degrees) and near-diffraction-limited beam quality along the vertical direction (i.e., the "fast" axis), whereas the divergence is much smaller (e.g., well below 10 degrees) along the periodic direction (i.e., "slow" axis) but with lower beam quality.

The spacing between adjacent emitters 108$^N$ ("emitter-to-emitter spacing" in FIG. 1) is often tens to hundreds of microns, with a wide range of possible fill factors (i.e., the fraction of the full width of the diode bar 100 that is filled with emitters 108$^N$). Each diode bar 100 is often around 1 cm wide in the periodic direction, although other widths are possible, and there may be a wide range of individual emitters 108$^N$ within this width (e.g., 10-200 emitters). The maximum total continuous-wave optical power per cm may be in the hundreds of watts. The width along the slow axis of an emitter 108$^N$ may also vary greatly between different diode bars.

The electrical-to-optical conversion efficiency of diode bars is often very high (e.g., 50-80% in modern devices), which is an important feature for efficient chemical processing, and the capital cost per watt is low compared to most other laser technologies. Using simple optics (e.g., small lenses aligned to emitters in the diode bars [not shown]) it is possible to collimate the beamlets 112$^N$ along the fast axis, resulting in a beam from the diode bar 100 that has rather small far-field divergence (e.g., sub-degree divergence on the fast axis, and less than 10 degrees on the slow axis).

By stacking many such diode bars (along with appropriate heat sinks), it may be possible to produce a high-power laser module that emits well in excess of 1 kW of continuous-wave optical power (and considerably higher peak powers if pulsed) per $cm^2$ of its emitting surface, along with a small far-field beam divergence as noted above.

Figure 2:
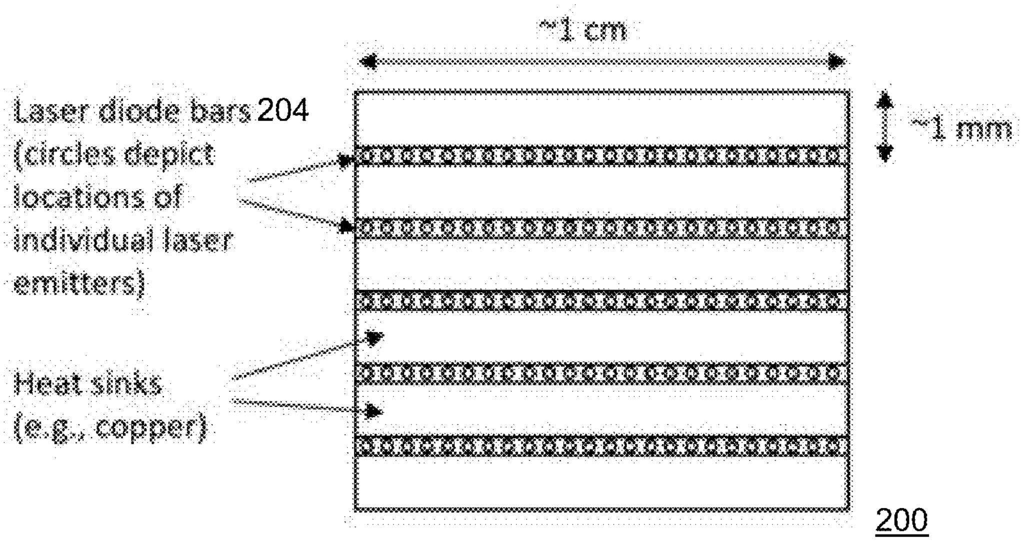
FIG. 2 presents an exemplary high-power laser module based on the diode bar of FIG. 1.
Figure 2:
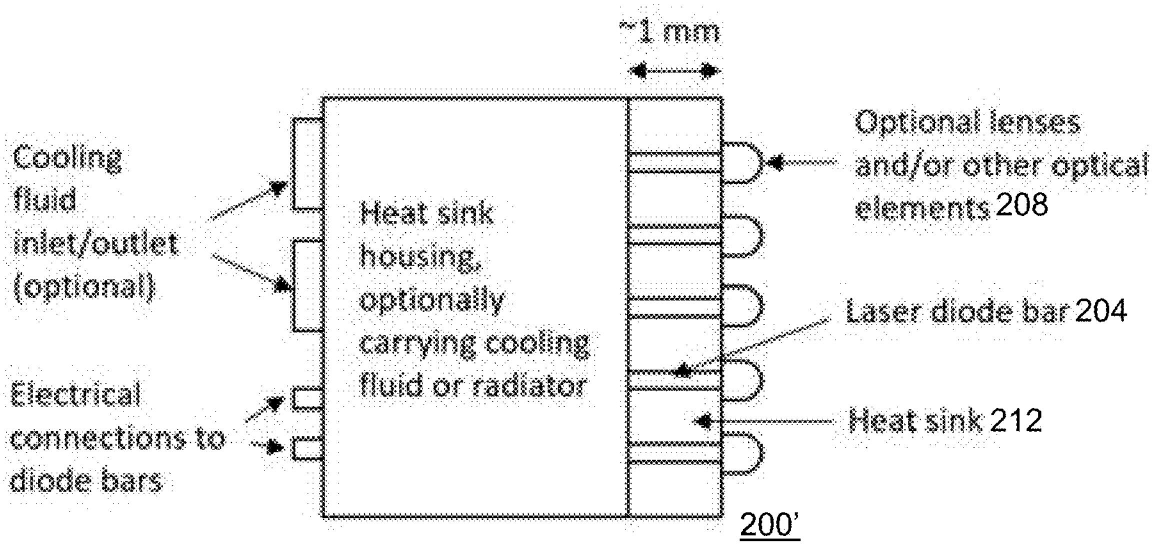

FIG. 2 depicts one example of a high-power laser module 200 based on diode bars 204, showing a view from the "front" (which contains the emitting facets of the individual semiconductor laser diode bars 204) and a view from the "side." In the side view, optional optical elements (e.g., lenses) 208 are shown affixed to the module 200. These optical elements 208 may be aligned to individual emitters or rows of emitters. The diode bars 204 are mounted in contact with appropriately sized heat sinks 212 (e.g., copper or other material with suitably high thermal conductivity) that may be connected to suitable structures for removing heat from the full assembly (e.g., microchannels carrying coolant, radiators for air-cooling, etc.). The electrical pads of the diode bars may be contacted using typical means (e.g., wirebonds, conductive paste, solder, direct metal-to-metal contact, etc.).

A similarly potent emitter may be formed using arrays of vertical-cavity surface-emitting lasers (VCSELs). VCSELs are individual laser emitters formed using a patterned semiconductor wafer, with the emitting apertures on one of the wafer surfaces rather than the cleaved wafer facets. Dense arrays of VCSELs may be produced, with individual VCSELs emitting an optical power ranging from, e.g., 1 mW to several hundred mW, and with laser wavelengths commonly in the near-infrared. The total optical power emitted per unit surface area of a VCSEL array can be quite high (e.g., ~1 kW/cm^2), and the electrical-to-optical conversion efficiency may also be high (e.g., above 50%). The capital cost per watt of VCSEL arrays may be quite low.

Figure 3:
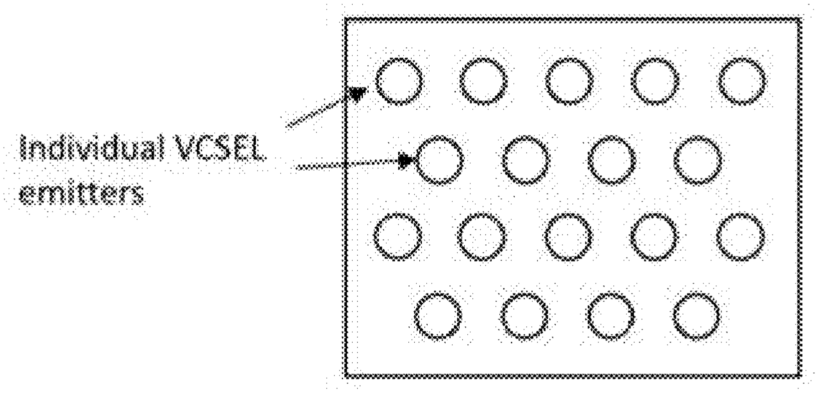
FIG. 3 presents an exemplary high-power laser module based on a VCSEL array.
Figure 3:
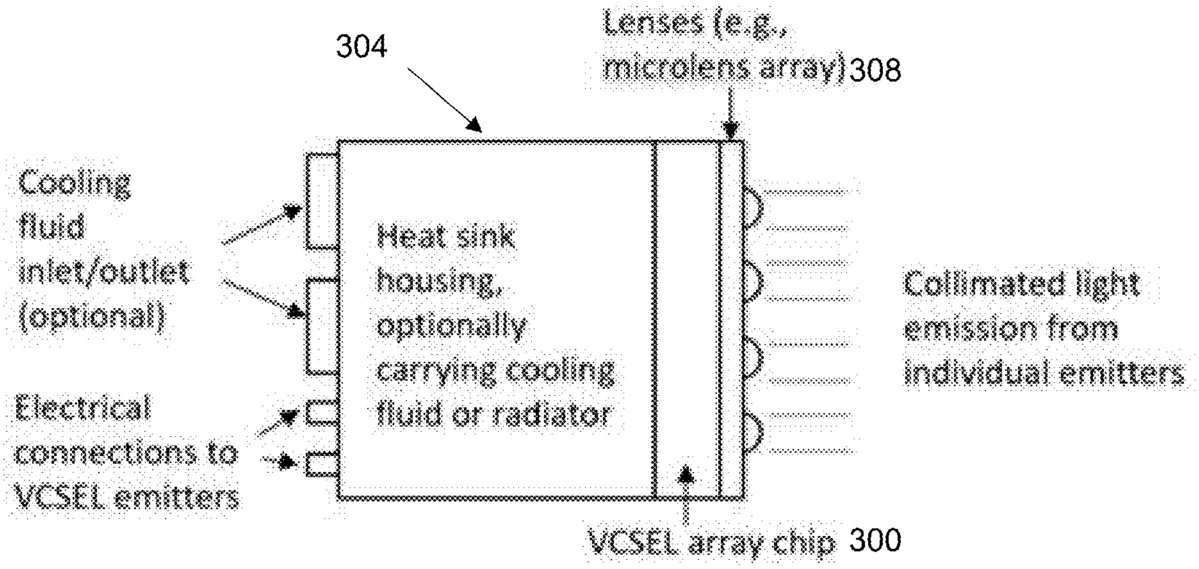

An exemplary high-power laser module based on a VCSEL array is shown in FIG. 3. The front view depicts the emitting surface of a VCSEL array 300, which is a piece of semiconductor wafer containing a two-dimensional array of VCSEL emitters. As shown in the side view, the VCSEL array 300 is mounted to a suitable heat sink 304 with suitable electrical connections. The emitting surface of the VCSEL array 300 is faced away from the heat sink 304. Lenses 308 (e.g., a microlens array) may be used to approximately collimate the beamlets, although this may not be necessary in all cases, as the divergence angle from some VCSELs may already be suitably small.

Feedstocks

Embodiments described herein are designed to deliver optical power rapidly into the bulk of a fluid, typically a gas. Such delivery may be very challenging by traditional means (e.g., because heat transfer into a gas via hot reactor walls is comparatively quite slow). Both low-cost laser modules described above may be the most efficient when near-infrared wavelengths are selected (e.g., in the wavelength range ~780 to ~1100 nm). Thus, it may be desirable to use feedstocks which have suitably strong absorption features in this wavelength window. Hydrocarbon-based feedstocks (e.g., methane, ethane) are of interest in this regard, as is water vapor. But in principle, any feedstock with suitable optical absorption features at the required temperatures, pressures, and optical path lengths may be used.

Laser Reactors

Figure 4:
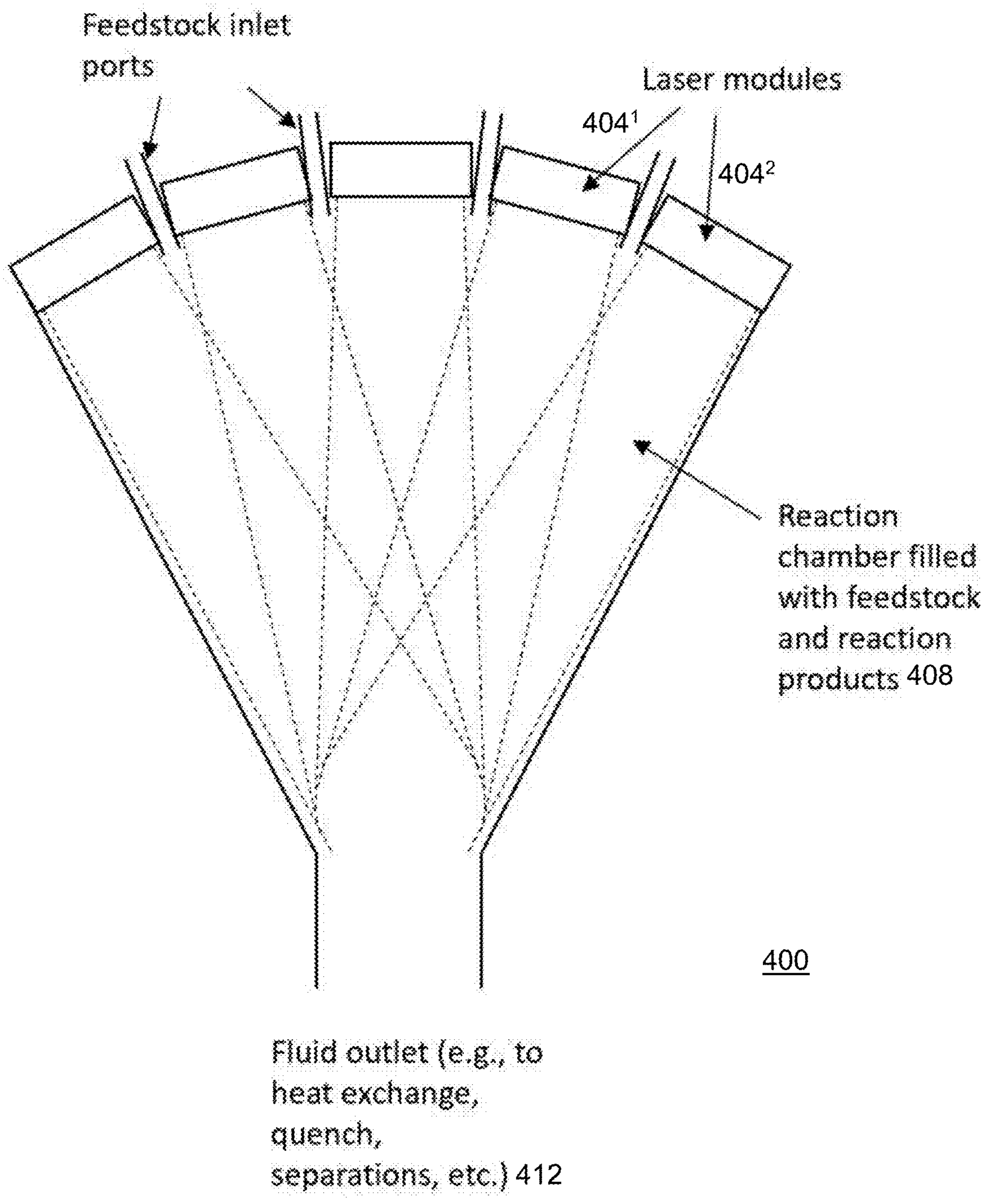
FIG. 4 shows one embodiment of a laser reactor for processing gaseous feedstocks.

One example of a laser-powered chemical reactor 400 for processing gaseous (or other fluid) feedstocks is shown in FIG. 4. Laser modules $\mathbf{404}^N$ (e.g., of the type described above using laser diode bars or VCSELs) with low beam divergence are arranged around a chamber 408 into which feedstock flows. The laser modules $\mathbf{404}^N$ emit light into the chamber 408 (dashed lines depict light beams) through suitable optical windows (not shown) in such a way that the beams may converge in certain areas of the reactor. By adjusting geometrical parameters (e.g., positions and orientations of laser modules, reactor shape, etc.) or optical parameters (e.g., using multiple wavelengths with different optical attenuation coefficients in the material) it is possible to tune the laser intensity profile within the reaction chamber 408.

If laser modules $\mathbf{404}^N$ based on laser diode bars are used, it may be advantageous for the reactor to be prism shaped (i.e., to have a footprint like that shown in FIG. 4, but with some substantial thickness out of the plane of the drawing) and to orient the laser modules $\mathbf{404}^N$ such that their fast axis lies in the plane of FIG. 4 (since with appropriate optics the fast axis of the emitters may have minimal far-field divergence; such an orientation may improve the ability to precisely guide the light, e.g., into a narrow taper like that shown in FIG. 4).

The reaction chamber 408 may be suitably pressurized such that a large fraction of the light is absorbed by the fluid before it reaches the outlet 412, or before the light scatters off other surfaces in the chamber 408. The feedstock may be injected near the laser modules $\mathbf{404}^N$ as shown in order to mitigate deposition of reaction products on optical windows or other optical surfaces. Reactor orientation, gravity, or suitable devices may also be used to control deposition. It may be furthermore useful for the optical windows between laser modules and reaction chamber (not shown) to be suitably coated, e.g., to improve transmission, to reflect thermal radiation back into the chamber 408 (for improved energetic efficiency of the reaction, and to minimize heat load on the laser modules, etc.).

Figure 5:
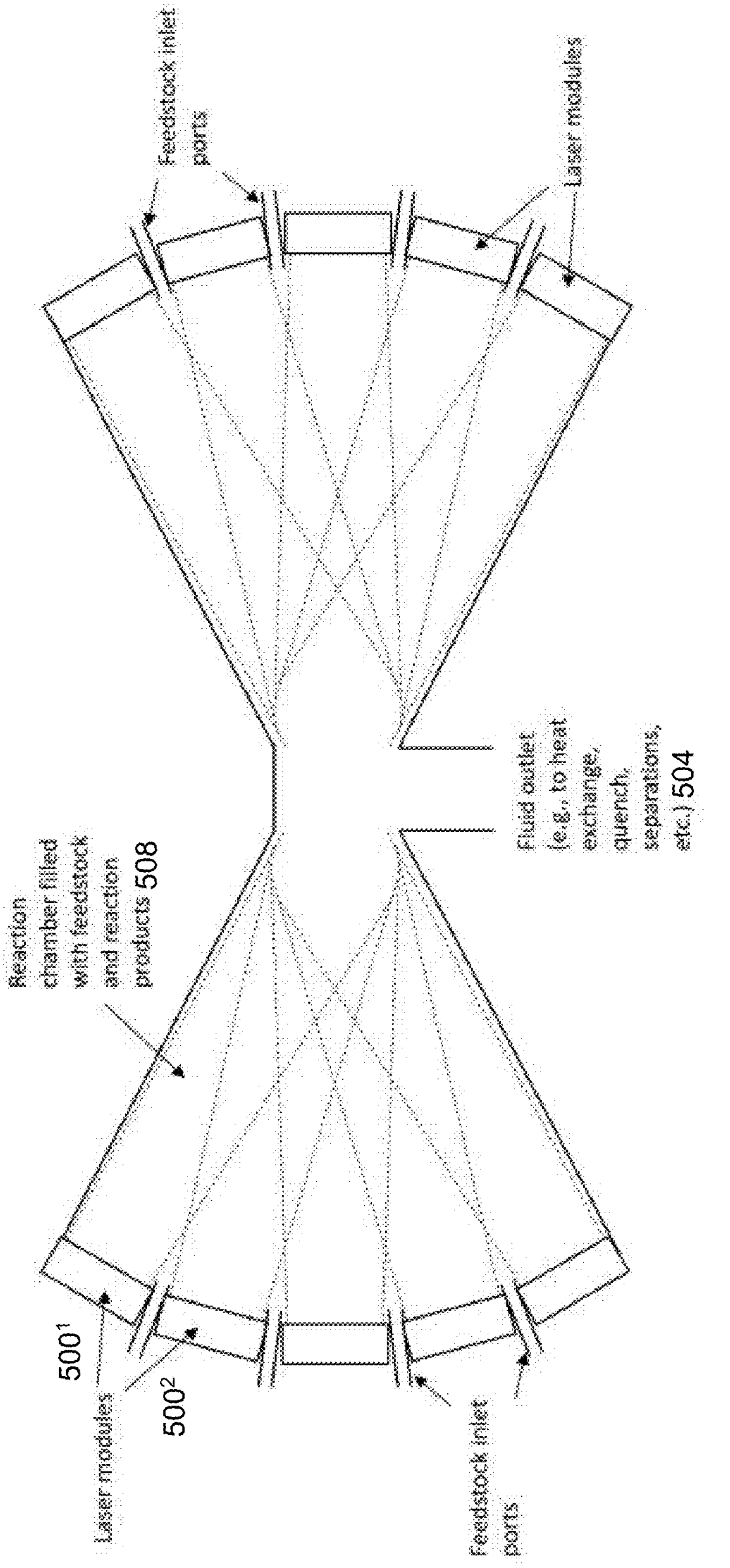
FIG. 5 presents another embodiment of a laser reactor for processing gaseous feedstocks.

An alternative reactor configuration is depicted in FIG. 5. In this concept, laser modules $\mathbf{500}^N$ may surround one or more fluid outlet ports 504, e.g., filling a large solid angle as seen from the outlet port 504 in FIG. 5; laser modules $\mathbf{500}^N$ may be diametrically opposed across the reaction chamber 508. Such a configuration may help increase the achievable laser power densities in certain areas of the reactor (e.g., near the feedstock outlet 504 in the center of the reactor depicted in FIG. 5), and/or the fraction of the laser light that is absorbed by the gas. In such a configuration, it may be useful to select sufficiently different laser wavelengths for diametrically opposed pairs of laser modules $\mathbf{500}^N$; optical coatings with suitable bandpass may then be used on the optical windows (not shown) to prevent opposed lasers from substantially heating each other.

Practically achievable optical intensities, e.g., with converging beams in the schemes depicted in FIG. 4 and FIG. 5, may be well in excess of 100 kW/$cm^2$. Such optical intensities are orders of magnitude higher than what may be achieved using, e.g., thermal radiation from the hot walls of a reactor.

Figure 6:
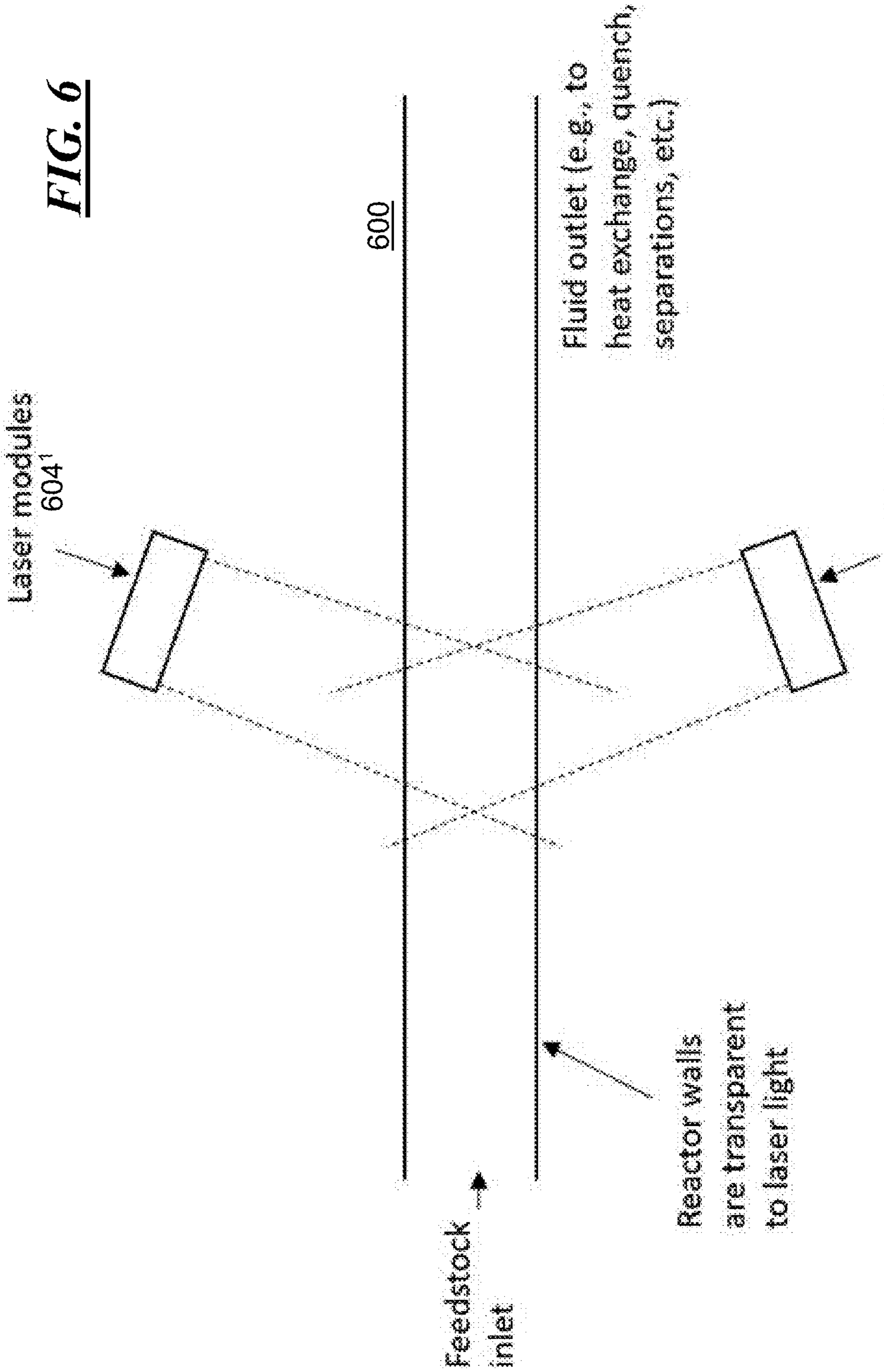
FIG. 6 depicts yet another embodiment of a laser reactor for processing gaseous feedstocks.

Yet another reactor configuration that may be advantageous under certain circumstances is depicted in FIG. 6. Appropriately pressurized feedstock gas (or liquid) is flowed through a tube 600 (running left-right in this depiction). The walls of the tube 600 may be transparent to laser light in certain regions. Laser modules $\mathbf{604}^N$ situated outside the tube 600 illuminate the fluids in the tube 600; to achieve high power density, a ring of laser modules $604^N$ may encircle the tube circumferentially (i.e., out of the plane of this figure).

The laser modules $604^N$ may be appropriately directed so as to not illuminate each other, and/or suitable optical coatings may be employed (e.g., in conjunction with selection of appropriately distinct wavelengths, as described previously) to mitigate mutual heating between diametrically opposed laser modules $604^N$. This reactor configuration may be advantageous for situations in which, e.g., the fluid feedstock should be exposed to a brief heating zone followed immediately by a quenching zone (which may be located immediately downstream of the laser apertures).

In any of the above concepts, it may further be useful to periodically or continuously remove deposits from optical surfaces (these deposits arising, e.g., from chemical reactions, contaminants, etc.). This may be accomplished by injection of suitable etchant gases into the reaction chamber, which may selectively etch deposits; etchant gases may be injected during a designated cleaning period, or they may be injected along with the processed feedstock. The etching process may be aided by laser heating (e.g., because the deposits are attached to optical surfaces within the beam path) or by a plasma discharge (e.g., an arc discharge, microwave plasma, etc.). Optical surfaces may also be cleaned mechanically, by applying a suitable etchant liquid to the surfaces, or by other schemes. It may be useful to control the temperature of optical surfaces during operation to mitigate buildup of deposits, e.g., by leveraging thermophoresis.

Laser-Based Methane Pyrolysis

One novel chemical process that may be enabled by the schemes described above is the laser-based pyrolysis of gaseous methane or natural gas. By heating methane to suitably high temperatures (e.g., above 1000 degrees Celsius), methane (and other species in natural gas) will begin to decompose, yielding hydrogen gas along with other hydrocarbon products (e.g., ethylene, acetylene) and possibly solid carbon. This process may be of interest as a low-cost source of clean hydrogen, as well as valuable hydrocarbons or solid carbon.

A challenge in performing this process is efficiently delivering the heat of reaction: the pyrolysis of methane is a highly endothermic process, but methane is in the gas phase. Delivering heat to a gas using a traditional approach like a heated furnace tube is a slow process requiring long residence times of the feedstock (this arises because thermal radiation from heated tube walls is rather weak, and because heat supplied to the fluid volume by contact with the hot tube surface is dimensionally disadvantaged). The effectiveness of a furnace tube is further reduced by coke buildup on the tube walls, which restricts fluid flow and further diminishes heat transfer to the feedstock. Catalysts may be used to lower reaction temperatures, but these tend to rapidly foul with solid carbon deposition, and do not circumvent the endothermic nature of the reaction.

A laser-based pyrolysis scheme may be advantageous for the pyrolysis of gaseous hydrocarbons because it delivers heat with high power density directly to the bulk feedstock (e.g., methane or natural gas). A suitable reactor geometry may resemble that of FIG. 4. Natural gas feedstock may be injected near the laser modules and heated by laser modules tuned to the near-infrared absorption features of gaseous hydrocarbons (e.g., near 890 or 970 nm). Feedstock may be pressurized (higher pressures, e.g., near or in excess of 10 bar, may be advantageous to ensure that most of the laser light may be absorbed within a few meters of propagation in the reaction chamber, reducing the needed reactor size). The feedstock may pyrolyze partially or completely, yielding valuable gas-phase products (e.g., hydrogen, ethylene, acetylene) and/or solid products (e.g., carbon black, acetylene black).

The reactor may be oriented such that gravity pulls any solids into an appropriate receptacle, and away from any optical surfaces. The product stream exiting the laser reactor may be sent through suitable heat exchangers to recover useful heat (e.g., to preheat incoming feedstock, to drive a heat engine, to supply other process heat, etc.). The product stream may also be appropriately separated (e.g., hydrogen may be separated and sold, or combusted to generate electricity; ethylene or acetylene gas may be separated and sold; residual hydrocarbon feedstock may be recycled to the input stream) using various means (e.g., selective membranes, pressure-swing adsorption, cryogenic distillation, etc.). It may be advantageous for the input feedstock to incorporate hydrogen gas; tailoring the hydrogen concentration may help skew the product distribution as desired.

Laser-Based Olefin Production

Another novel chemical process that may be enabled by the laser-based chemical reactor concepts described above is laser-based production of olefins from feedstocks like ethane, naphtha, or other hydrocarbons. This process would be a clean, electrified alternative to traditional steam cracking.

Traditional steam crackers carry out the pyrolysis of alkanes (e.g., ethane) to olefins (e.g., ethylene, propylene). The pyrolysis reaction initiates at high temperatures, but if high temperature is held for too long, the olefins themselves start to degrade to products like acetylene and soot. Hence the highest yields of olefins are obtained when the process gas is very rapidly ramped and quenched; a typical steam cracker ramps its process gas from ~600° C. to ~850° C. over a few hundred milliseconds, and quenches back down to 500-600° C. within another hundred milliseconds or so.

In order to achieve such a rapid temperature ramp with high feedstock throughput—a task which is made more challenging owing to the considerable enthalpy of reaction (>100 kJ/mol $C_2H_6$) that must be delivered, as well as the rather low thermal conductivity of the gas—a steam cracker will push the process gas near the speed of sound through long (10-100 m), narrow (~10 cm diameter) "cracking coils" maintained at a high temperature (e.g., 1000° C.) by a firebox.

One drawback of this scheme is its susceptibility to coke deposition. Since the coils must be particularly hot (hotter than the process gas) in order to rapidly supply heat, they act as excellent nucleation sites for coke deposition. And since coke is a poor thermal conductor, the temperature of the coils must be further increased once coke starts to deposit. Increasing temperature decreases coil lifetime, and this can only continue for so long before it becomes economically advantageous to shut down the entire steam cracker to clean out the coke. The shutdown may cost two days and may happen once every few weeks to few months depending on the length of coil (shorter coils may reduce residence time and improve yield, but may require higher temperatures and therefore coke faster). Decoking shutdowns are a major operational expense to go along with the capital expense from the massive fireboxes, long coils, and powerful pumps that drive the large fluid impedance.

A laser-heated steam cracker could circumvent these issues using a laser-based reactor concept (e.g., as shown in FIG. 4, FIG. 5, or FIG. 6, with, e.g., ethane and steam as a feedstock) in place of the firebox and cracking coils in a traditional steam cracker. A laser module may be able to deliver an average intensity of, e.g., 1 $MW/cm^2$ to the gaseous steam/hydrocarbon mixture, whereas the traditional cracking coil surfaces might deliver only 10 $W/cm^2$. Since the coils radiate in the mid-infrared, whereas the near-infrared light from the laser modules might be tuned to water absorption at 950 nm where the optical cross-sections might be ~300× lower, the relative volumetric power delivery advantage of the laser might be roughly estimated as (1 MW/10 W)/300, or roughly 300×. This is a sizeable margin that could allow a laser reactor to dispense with long, narrow coils and reduce pumping requirements.

The walls of the laser reactor need not be hot, and could be coated with arbitrary anti-coking materials (whereas coatings on coils need good thermal conductors), and the laser reactor tubes could be relatively short and wide; the laser reactor would thus be far less affected by coke deposition, mitigating the operational losses associated with decoking while still permitting very short residence times for high yield. The laser modules may alternatively be operated in a pulsed mode to deliver sub-millisecond pulses instead of continuous-wave power (note that the achievable peak powers from laser diodes often significantly exceed the achievable continuous-wave powers); the pulsed configuration may improve product distributions.

An even more minimal version of laser-assisted alkane cracking eliminates the steam dilution apparatus entirely, further saving capital and operating expenses. One function of the steam in the traditional cracker is to act as a diluent, which may be helpful since low hydrocarbon partial pressures favor the unimolecular decomposition reactions over the unwanted secondary multi-molecular reactions. Simply lowering the pressure of the ethane is impractical in traditional systems because the pressure drop across the coils is so large-perhaps as high as 1 bar in some cases. Another function of the steam is to combat coking. These functions may no longer be needed in a laser reactor, in which both the pressure drop and the coking (and the extent to which coking may be important, as long as it does not deposit on the optical window) are greatly reduced. Because the laser-based cracking apparatus is electrified and does not require, e.g., a firebox, it may be possible to operate it intermittently, which may lead to cost-of-electricity advantages (especially, e.g., with electricity from renewable sources).

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of various implementations or techniques of the present disclosure. Also, a number of steps may be undertaken before, during, or after the above elements are considered.

Having been provided with the description and illustration of the present application, one skilled in the art may envision variations, modifications, and alternate embodiments falling within the general inventive concept discussed in this application that do not depart from the scope of the following claims. This approach could be used in any space where there are objects that are human rated, but the set of objects remains minimally covered by human ratings. The overall concept is highly generalizable, especially in the space of security and in domains where human input is highly valued.

What is claimed is:

1. A laser reactor for processing gaseous feedstocks, the reactor comprising:

a reaction chamber having an intake for receiving a gaseous feedstock, a plurality of optical windows, and an outlet; and a plurality of laser modules, wherein each laser module of the plurality of laser modules is configured to emit laser light into the chamber through an at optical window of the plurality of optical windows and thereby convert the gaseous feedstock into at least one reaction product, and wherein the plurality of laser modules are configured to surround the reaction chamber and each of the plurality of optical windows are optically coated to block a predetermined range of frequencies.

2. The reactor of claim 1 further comprising a receptacle for collecting the at least one reaction product as it is formed.

3. The reactor of claim 1 wherein the laser module is operated in a pulsed mode.

4. The reactor of claim 1 wherein the laser module is an array of semiconductor laser diode bars or a vertical-cavity surface-emitting laser array.

5. The reactor of claim 1 further comprising a mechanism for adjusting the pressure of the reactor.

6. The reactor of claim 1 wherein the intake is juxtaposed with the window.

7. The reactor of claim 1 wherein the intake is juxtaposed with the window.

8. The reactor of claim 1 wherein the reaction chamber is transparent.

9. The reactor of claim 1 wherein the laser light is near-infrared.

10. The reactor of claim 1 wherein the gaseous feedstock comprises one or more of methane, ethane, hydrogen or steam.

11. The reactor of claim 1 further comprising a heat exchanger at the outlet.

12. A method for laser processing of gaseous feedstocks, the method comprising: providing the laser reactor of claim 1; admitting a gaseous feedstock to the reaction chamber via the intake; and applying laser light to the gaseous feedstock through an optical window of the plurality of optical windows to form at least one reaction product.

13. The method of claim 12 further comprising collecting, in a receptacle, the at least one reaction product as it is formed.

14. The method of claim 12 further comprising increasing the pressure of the reaction chamber to improve the absorption of the laser light by the gaseous feedstock.

15. The method of claim 12 further comprising admitting an etchant gas to the reaction chamber to facilitate the cleaning of the optical window.

16. The method of claim 12 wherein the feedstock comprises one or more of methane, ethane, or naphtha.

* * * * *